(12) United States Patent
Lemoine

(10) Patent No.: US 10,566,178 B2
(45) Date of Patent: Feb. 18, 2020

(54) SENTINEL SIGNAL FOR ADAPTIVE RETENTION TIME IN TARGETED MS METHODS

(71) Applicants: DH TECHNOLOGIES DEVELOPMENT PTE. LTD., Singapore (SG); Université Claude Bernard Lyon 1, Villeurbanne (FR); Centre National de la Recherche Scientifique, Paris (FR); École Normale Supérieure de Lyon, Lyons (FR)

(72) Inventor: Jerome Lemoine, Lucenay (FR)

( * ) Notice: Subject to any disclaimer, the term of this patent is extended or adjusted under 35 U.S.C. 154(b) by 67 days.

(21) Appl. No.: 15/780,281

(22) PCT Filed: Nov. 24, 2016

(86) PCT No.: PCT/IB2016/057083
§ 371 (c)(1),
(2) Date: May 31, 2018

(87) PCT Pub. No.: WO2017/093861
PCT Pub. Date: Jun. 8, 2017

(65) Prior Publication Data
US 2019/0371586 A1 Dec. 5, 2019

Related U.S. Application Data

(60) Provisional application No. 62/261,498, filed on Dec. 1, 2015.

(51) Int. Cl.
*H01J 49/26* (2006.01)
*H01J 49/00* (2006.01)

(52) U.S. Cl.
CPC ...... *H01J 49/0045* (2013.01); *H01J 49/0031* (2013.01)

(58) Field of Classification Search
CPC .................... H01J 49/0045; H01J 49/0031
(Continued)

(56) References Cited

U.S. PATENT DOCUMENTS 9,170,263 B2 * 10/2015 Lemoine ............ G01N 33/6848
9,513,232 B2 * 12/2016 Cox .................... H01J 49/0031
(Continued)

FOREIGN PATENT DOCUMENTS

JP      2003-172726 A      6/2003

OTHER PUBLICATIONS

International Search Report and Written Opinion for PCT/IB2016/057083, dated Feb. 28, 2017.

*Primary Examiner* — Nicole M Ippolito
(74) *Attorney, Agent, or Firm* — John R. Kasha; Kelly L. Kasha; Kasha Law LLC

(57) ABSTRACT

A plurality of MRM transitions to be used to monitor a sample are received and divided into two or more contiguous groups. At least one sentinel transition is selected in each group that identifies a next group of the two or more contiguous groups that is to be monitored. A first group of the two or more contiguous groups is placed on a duty cycle list of the tandem mass spectrometer. One or more compounds are separated from the sample and ionized, producing an ion beam. A series of MRM transitions read from the duty cycle list are executed on the ion beam by the tandem mass spectrometer. When at least one sentinel transition of the first group is detected, a next group identified by the sentinel transition is placed on the list.

15 Claims, 9 Drawing Sheets

(58) Field of Classification Search
USPC .............. 250/281, 282, 283, 287, 288, 290
See application file for complete search history.

(56) References Cited

U.S. PATENT DOCUMENTS

| | | |
|---|---|---|
| 2009/0008542 A1 | 1/2009 | Sumiyoshi |
| 2010/0301201 A1 | 12/2010 | Gordon et al. |
| 2013/0289894 A1 | 10/2013 | Cox et al. |
| 2014/0014833 A1 | 1/2014 | Sekiya |
| 2016/0365236 A1* | 12/2016 | Green ................ H01J 49/0031 |

* cited by examiner

SENTINEL SIGNAL FOR ADAPTIVE RETENTION TIME IN TARGETED MS METHODS

CROSS REFERENCE TO RELATED APPLICATION

This application claims the benefit of U.S. Provisional Patent Application Ser. No. 62/261,498, filed Dec. 1, 2015, the content of which is incorporated by reference herein in its entirety.

INTRODUCTION

Various embodiments relate to the analysis of substances with a mass spectrometer. In particular, various embodiments relate to the detection of and relative or absolute quantification of substances by mass spectrometry coupled to hyphenated techniques. Successive groups of substances of interest are monitored as a function of successive detection of signals, for example.

The coupling between a separation system and a mass spectrometer has been used for many years for the detection and quantification of substances in complex mixtures. Just as a spectrophotometer, for example, the mass spectrometer can be used as a selective detector of substances separated by chromatography or capillary electrophoresis. Substances detected can be small organic molecules such as drugs, doping molecules, pesticides, metabolites, proteins, or peptides, for example. In general, methods of detection and quantification using a coupling between a mass spectrometer and a separation technique use a fragmentation step (tandem mass spectrometry, mass spectrometry-mass spectrometry (MS-MS), MS2, MSn). Usually, the fragmentation is obtained by a process of collision between ions and an inert gas but may also result from interaction with electrons, photons, or a surface. This fragmentation step is sought to ensure the highest possible level of detection specificity thanks to the combination of information between the intact species and the relative intensities of its fragments or product ions. The second level of specificity is provided by the relative or absolute retention time of the substance in the separation process.

The most common approach to perform detection and/or quantification of a substance by mass spectrometry is the so-called targeted approach. Though any instrument allowing MSn experiment is suitable, the targeted method is mainly performed on a triple quadrupole mass spectrometer which results from the assembly of three quadrupoles. In this mode of use, the mass spectrometer is set to record the signal associated with an event called a transition where a precursor ion (often corresponding to the whole substance) is filtered in a first quadrupole then fragmented in quadrupole 2 and one or successively many product ions are filtered in the quadrupole 3. It is important to note here that the signal associated with a transition is more intense when the mass spectrometer remains on the observation of this transition.

When multiple transitions are observed for the same molecule, and even more importantly when multiple transitions are observed for several molecules to quantify, it is necessary to adjust the observation time to ensure perfect definition of the shape of the chromatographic or electrophoretic peaks. It is agreed that a minimum of 10 measurement points is typically required to draw such a peak to ensure the quantification accuracy and satisfactory accuracy.

Thus, if a chromatographic peak has a baseline width of 10 seconds and the observation time (dwell time) of a transition is 10 milliseconds, then it will be possible to monitor up to 100 transitions since the total observation time thereof is 100×10 milliseconds=1 s. If two transitions must be observed by molecules, no more than 50 molecules can be detected and quantified during analysis, or 100/n if n molecules transitions to be observed by molecules.

In very many situations, whether basic or applied research, it is desirable to observe hundreds of substances to be quantified. This is, for example, the case in the detection of and quantification of pesticides in environmental matrices (water and soil) or in food or in biological fluids. Another well-known context is the targeted detection and quantification of hundreds to thousands peptides in proteomics-based approaches. This context can be clinical evaluation studies of biomarker candidates or the more fundamental context of systems biology. In this case, the limit imposed by the minimum number of measurement points to properly define the shape of a peak needs to be circumvented by limiting the observation time of a transition. Thus, instead of programming the monitoring of a transition for the duration of the separation method, it is followed only in a limited time window. This observation time window can be relatively large and gather the necessary transitions followed by several molecules. The optimal and often retained strategy is, however, to record the specific transitions of a substance only around its retention time window. Different trade names refer to this process: scheduled multiple reaction monitoring (MRM) by AB Sciex, timed MRM by Thermo, dynamic MRM by Agilent, for example. However, multiple causes can lead to a drift of retention time. The cause can be voluntary when, for example, in liquid chromatography the experimenter changes the slope of the gradient, the column length, the composition of the mobile phase, or the particle diameter. The cause may also be independent of the experimenter and results from column overloading, partial blockage of the column, temperature variation of the mobile phase.

Hence, any variation in retention time increases the possibility that the molecule is not detected in its programmed retention time window. Thus, to take into account these potential variations of retention times, the width of the observation window is always wider than the width of the elution peak of the substance, the more often a factor of two to three. This precaution has the effect of restricting the number of transitions and therefore the observable substances in a given unit of time. Similarly, the width of these windows should be reconsidered when the flow rate of the mobile phase will be radically changed by passing from a conventional HPLC mode to ultra HPLC mode, or vice versa. Finally, the timing of the observation windows should also be checked as soon as the experimenter changes the stationary phase, because, even for a similar type of octadecyl (C18) graft, the grafting chemistry and the chemical nature of the beads affect the selectivity of the column that can result in retention time inversion.

Finally, another drawback of conventional methods is that they cannot be easily transferred to another instrument or analysis site without performing a first adjustment of the experiment retention time.

Recently, new methods have been introduced to facilitate the transfer method of a device to another or between different sites. The first method proposed by Escher et al. describes a method for normalizing the peptide retention time against other reference peptides in order to assign them a universal retention time index. The claimed advantage of this method (iRT) is that it can better predict the empirical retention times of peptides compared to a prediction algorithm. The process is however limited in that a first calibration step is always necessary when the method is transferred to another system. Also, this process does not significantly reduce the width of the detection windows, which remains at a minute in most studies using this method. Recently, Domon et al. have proposed a method for improving the preceding iRT strategy for on-the-fly correction of retention time. In this method, ideally several compounds (peptides in this study) are used as anchors and distributed uniformly throughout the chromatogram in order to detect possible retention time drifts. In this method, two anchors eluted consecutively are used to recalculate a possible correction of the gradient slope. This process can avoid changing the observation time windows during a voluntary change in the gradient slope or flow, or when a variable dead volume causes a delay more or less in the elution of the first compound. However, this method has several limitations. It cannot be applied in the case of a non-linear distortion of the gradient caused, for example, by a transient rise in pressure. The correction occurs only when the second anchor is detected, so the eluted substances, before this second anchor, may not be detected if its retention time moves. Finally, this method still requires the use of programmed detection windows. Thus, in the study described by Domon et al., detection windows at least on the order of one or two minutes are used. In the study described by Guo et al., even larger detection windows were used for complex cellular extracts.

Thus, state of the art methods used to increase the multiplexing capabilities of relative or absolute assay based on a separation system coupled to a mass spectrometer systematically are generally of two types. In the first type of method time segments are used where specific transitions of eluted substances between two retention times are programmed. In the second type of method, a series of overlapping time windows framing the retention times of the targeted substances are used. These windows are distributed according to the chronological elution order of the targeted substances.

It is therefore the object of this disclosure to provide an alternative method for the analysis of multiple substances in complex mixtures.

SUMMARY

At the start of the analysis, the mass spectrometer is set to detect a first group i of transitions that contains a sentinel signal i. The detection of the sentinel signal i in the group of transitions i, considering the i signal is defined by one or more transitions above a predetermined threshold, opens a new group i+1 of transitions which itself contains a sentinel signal i+1, which, when it is detected, in turn will open up a new group i+2 transitions which itself contains a sentinel i+2 signal. In a group of transitions, several transition characteristics of substances eluted immediately prior to a sentinel signal are present in the next group to ensure continuity of detecting substances until they are completely eluted. Therefore, electrophoretic or chromatographic peaks are perfectly defined.

Within each group, the transitions can be arranged in a completely random order as the number of transitions within a group is only conditioned by the difference of elution time width between two sentinel signals.

Thus, the Sentinel process is radically different from all conventional methods, since this process does not use any time window to observe transitions, i.e., neither time window defined by two empirical or calculated indexed retention time, nor a time window corrected in real time.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
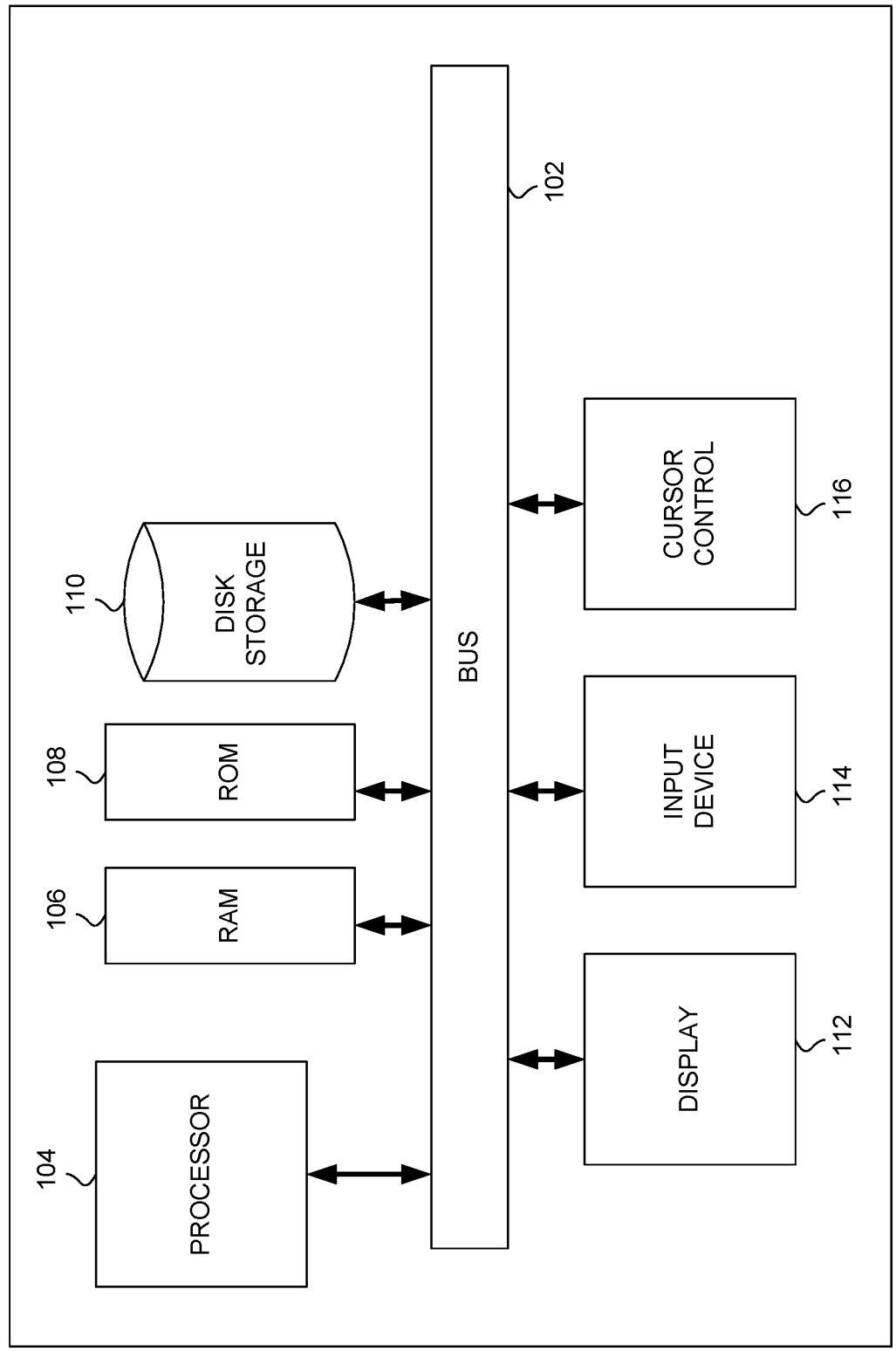
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Triggering Contiguous Groups of Transitions

Systems and methods for triggering a group of multiple reaction monitoring (MRM) transitions from a series of contiguous groups when at least one sentinel transition of the group is detected as part of a previous group are described in this detailed description of the invention. In this detailed description, for purposes of explanation, numerous specific details are set forth to provide a thorough understanding of embodiments of the present invention. One skilled in the art will appreciate, however, that embodiments of the present invention may be practiced without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of embodiments of the present invention.

As described above, one targeted approach to the detection and/or quantification of a substance by mass spectrometry is called multiple reaction monitoring (MRM). MRM can also be referred to as selected reaction monitoring (SRM). In these methods, precursor ion and product ion pairs, called transitions, which are used to identify or quantify known compounds, are predefined for a particular experiment. A tandem mass spectrometer is then used to repeatedly interrogate each of these transitions as compounds are separated from a mixture using a separation device. The tandem mass spectrometer interrogates each transition by selecting and fragmenting the precursor ion of the transition and then analyzing the resulting fragments for the intensity of the product ion of the transition. The tandem mass spectrometer reads the predefined transitions from list, for example. The list can be called a duty cycle list, for example. The tandem mass spectrometer monitors each transition of the predefined transitions during each cycle of a plurality of time cycles. The completion of the plurality of time cycles can be referred to as one acquisition.

Each transition meant to identify or quantify a particular known compound must be monitored while the known compound is separating or eluting. In addition, in order to provide enough resolution to identify or quantify the known compound, the transition must be monitored many times while the known compound is separating or eluting. In other words, each separation of the known compound occurs over time and has an intensity versus time shape that is referred to a separation peak or elution peak. In order to provide enough resolution to identify or quantify each known compound, each transition must be monitored at enough times or data points across the elution peak. If each transition is monitored at enough times or data points across the elution peak, a product ion peak with a similar shape to the elution peak is traced out for the transition. This product ion peak is then used to identify or quantify the compound.

In addition, more than one transition may be need to identify or quantify a known compound. As a result, many transitions may be monitored many times during each elution peak. However, since the tandem mass spectrometer takes time to monitor each transition, only a finite number of MRM transitions can be monitored during each elution peak.

The mass spectrometry industry has developed various methods to improve or maximize the number of MRM transitions that can be detected in one analytical workflow or during one acquisition. Currently, for example, thousands of different MRM transitions can be handled in a single analytical workflow or acquisition.

As described above, one exemplary method to improve or maximize the number of MRM transitions that one could detect in an analytical workflow is called scheduled MRM. In scheduled MRM, each MRM transition defined in the workflow has a retention time associated it. Consequently, each MRM transition is monitored only around its retention time. Therefore by scheduling the MRM transitions, the maximum number of transitions that are monitored at any point in time during an acquisition is optimized. In other words, not all MRM transitions need to be monitored for the entire acquisition time. This approach provides more data points across an elution peak and, therefore, better precision, sensitivity, and accuracy.

However, scheduled MRM has an important limitation. It is dependent on the accuracy and absolute value of the retention time used for each transition. Whenever the separation device changes or the gradient of separation changes, the retention time for each transition must be recomputed. This becomes particularly cumbersome when workflows include thousands of MRM transitions. This also makes it difficult to use scheduled MRM workflows across separation devices produced by different manufacturers that have different elution rates.

In various embodiments, systems and methods are provided to limit the number of MRM transitions monitored at any one time without requiring the re-computation of retention time for each MRM transition, whenever the separation device changes or the gradient of separation changes. In these systems and methods, the MRM transitions to be used for an entire acquisition are ordered according to an expected retention time. The ordered MRM transitions are then divided into contiguous groups with different expected retention time ranges. In each group, at least one transition is selected as a sentinel transition. The sentinel transition in each group is used to identify the next group and trigger it for monitoring.

During acquisition, a first group of transitions is selected for monitoring. This is, for example, the group with the earliest expected retention time. When at least one sentinel transition in the first group is detected by the tandem mass spectrometer, the next group of transitions identified by the at least one sentinel transition is added to the list of transitions monitored by the tandem mass spectrometer. In other words, at least one sentinel transition in each group is used to trigger the transitions in the next contiguous group.

A group of transitions can also be removed from monitoring. For example, once at least one sentinel transition in the next contiguous group is detected, the transitions in the first group can be removed from monitoring.

As a result, by using sentinel transitions to trigger the addition and subtraction of MRM transitions from monitoring the overall number of MRM transitions being monitored at any one time is reduced. In addition, because the groups of transitions are not dependent on a specific retention time, workflows based on these systems and methods can be used without modification whenever the separation device changes or the gradient of separation changes.

Figure 2:
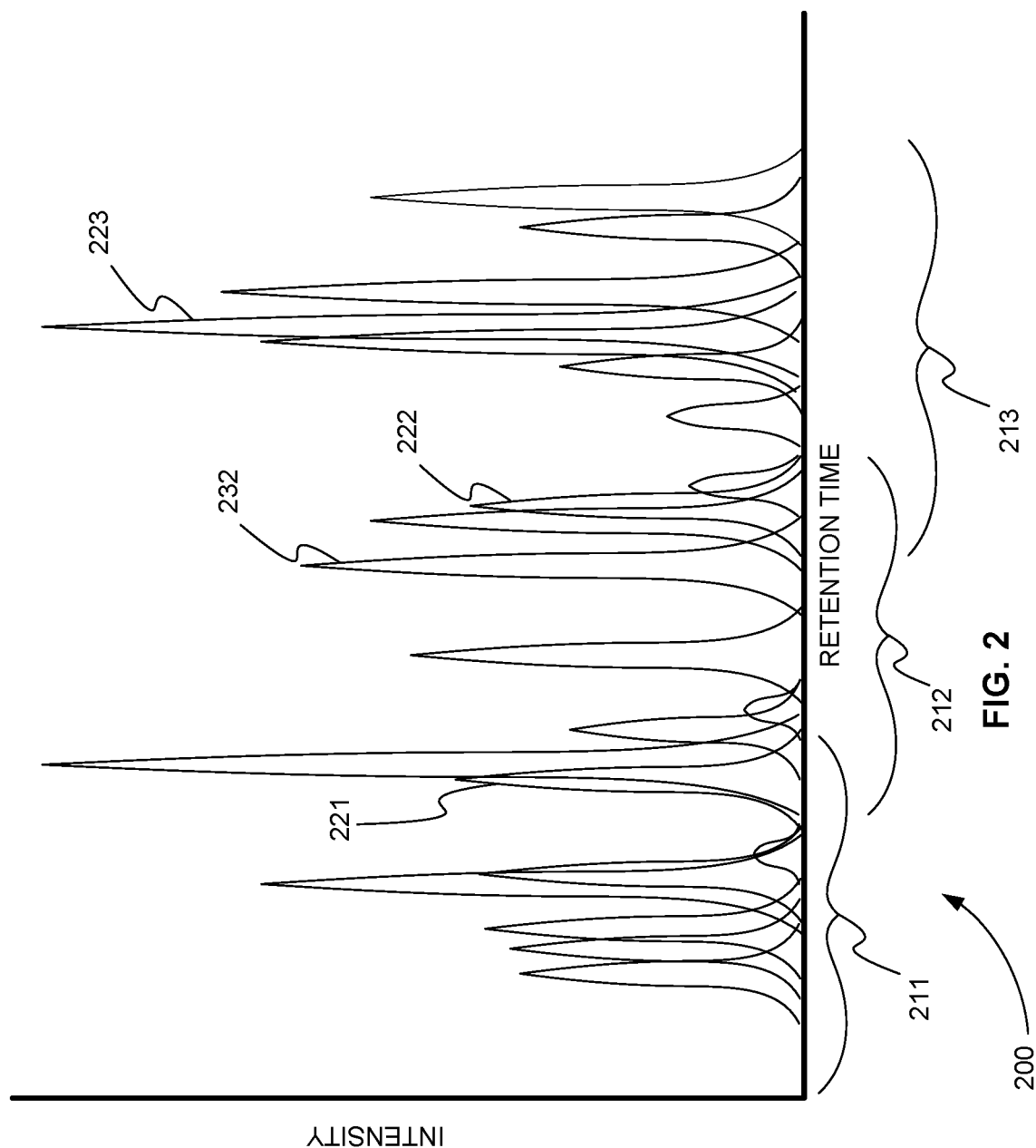
FIG. 2 is an exemplary total ion current (TIC) chromatogram plot showing how MRM transitions are grouped based on their corresponding expected product ion chromatographic peaks, in accordance with various embodiments.

FIG. 2 is an exemplary total ion current (TIC) chromatogram plot 200 showing how MRM transitions are grouped based on their corresponding expected product ion chromatographic peaks, in accordance with various embodiments. In plot 200 the expected intensity versus retention time chromatographic peaks of 22 product ions are plotted. These 22 product ion peaks correspond to 22 MRM transitions (not show). The 22 product ion peaks are plotted in plot 200 as a TIC chromatogram and are, therefore, ordered according to increasing retention time. The product ion peaks, in turn, order the corresponding MRM transitions by retention time. The actual or absolute value of the retention times is not important. It is the order that is important.

Once the 22 MRM transitions are ordered based on the 22 product ion peaks, the MRM transitions are grouped. In practice, groups are created, for example, by including in each group or across two groups the maximum number of MRM transitions that can be monitored with the desired resolution across an elution peak. This maximum number could be 200 MRM transitions, for example. In other words, the purpose of the groups is to limit the number of MRM transitions being monitored at any one time in order to maintain the resolution necessary across any one elution peak. After meeting this requirement, the groups can be selected in any way. The groups, however, also have to be contiguous to ensure that all MRM transitions are monitored at some point.

For purposes of illustration here, the 22 MRM transitions corresponding to the 22 product ion peaks are grouped more or less evenly into early-eluting, mid-eluting, and late-eluting groups. For example, group 211 includes the early-eluting product ion peaks, group 212 includes the mid-eluting product ion peaks, and group 213 includes the late-eluting product ion peaks. Groups 211-213 are contiguous.

Groups 211-213, as shown, can also include overlapping regions. If a previous group is removed as soon as a next group is added, the overlapping product ion peaks and corresponding overlapping MRM transitions ensure that product ion peaks near the end of the previous group are fully defined. Another method of ensuring that product ion peaks near the end of the previous group are fully defined is to simply allow two groups to be monitored at any one time, for example.

Groups are monitored or not monitored based on sentinel transitions. In each group at least one sentinel transition is selected from the MRM transitions in the group. Any transition of the MRM transitions in a group can be selected as the at least one sentinel transition. For example, the at least one sentinel transition can be selected from the beginning, middle, or end of the group. In addition, more than one sentinel transition can be selected for each group, but each group that has a following group must have at least one sentinel transition. Note the last group in the series need not have a sentinel transition.

Also, different types of sentinel transitions can be used. The primary type of sentinel transition is an MRM transition that identifies or triggers the next group for monitoring. This type of sentinel transition is, for example, a start sentinel transition. In various embodiments, another type of sentinel transition is a stop sentinel transition. This type of sentinel transition is not necessary, but can be used to trigger the removal of a previous group from monitoring, for example. Stop sentinel transitions are discussed more below.

In plot 200, peak 221 is selected as the at least one sentinel transition for group 211, peak 222 is selected as the at least one sentinel transition for group 212, and peak 223 is selected as the at least one sentinel transition for group 213, for example. Therefore, the MRM transition corresponding to peak 221 identifies or is used to trigger the monitoring of group 212. The MRM transition corresponding to peak 222 identifies or is used to trigger the monitoring of group 213. If there were a next group after group 213, the MRM transition corresponding to peak 223 would identify or would be used to trigger the monitoring of that group.

Once a group of MRM transitions is triggered it should not be monitored for the entire acquisition. Otherwise the number of MRM transitions monitored at any one time would not be limited near the end of the acquisition if no groups of transitions were removed. As described above, once at least one sentinel transition in the next contiguous group is detected, the transitions in the previous group can be removed from monitoring.

For example, the MRM transitions corresponding to the product ion peaks of group 211 are monitored first. When peak 221 corresponding to the at least one sentinel transition of group 211 is detected above a certain threshold intensity, the MRM transitions of group 212 are triggered for monitoring. As a result, for some time the MRM transitions corresponding to groups 211 and 212 are monitored together. However, when peak 222 corresponding to the at least one sentinel transition of group 212 is detected above a certain threshold intensity, not only are the MRM transitions of group 213 triggered for monitoring, but the MRM transitions of group 211 are removed from monitoring. In this way, the at least one sentinel transition of group 212 corresponding to peak 222 acts as both a start and stop sentinel. It acts as a start sentinel by triggering the monitoring of the MRM transitions of group 213, and it acts as a stop sentinel by removing the monitoring of the MRM transitions of group 211.

This scheme works well when the sentinel transition corresponding to peak 222 is near the end of group 212. If the sentinel transition had a retention time near the beginning of group 212, the MRM transitions of group 211 might be removed before the MRM transitions near the end of group 211 had fully defined their product ion peaks. Of course one solution, as described above, is to include large overlap regions between groups. Another solution is to always pick sentinels near the end of each group.

A third solution, alluded to above, is to have specifically defined stop sentinels. For example, group 212 can include a stop sentinel transition corresponding to peak 232. When peak 232 is detected above a certain intensity threshold level, the MRM transitions of group 211 are removed from monitoring. Using start and stop sentinels can further limit the number of MRM transitions monitored over the entire acquisition. For example, during the time period between peak 232 and peak 222 only the MRM transitions of group 212 are monitored.

Using an MRM transition to trigger a group of other MRM transitions has been described previously. For example, U.S. Pat. No. 8,026,479 (hereinafter the "479 patent") describes using an MRM transition to trigger a group of confirmatory MRM transitions. In other words, then a triggering MRM transition is detected, a group of one or more other confirmatory MRM transitions expected at the same retention time are triggered to confirm the presence of the compound represented by the triggering MRM transition. The confirmatory MRM transitions may include different precursor ions, but they are for the same target compound triggering MRM transition. In other words, the confirmatory MRM transitions are selected for the same elution peaks as the triggering MRM transition.

In contrast, various embodiments described herein use a triggering MRM transition, called a sentinel transition, to trigger a group of MRM transitions that include at least one transition targeting a retention time and an elution peak other than the retention time and elution peak of the sentinel transition. In other words, the triggering MRM transition of the '479 patent is designed to trigger a group of transitions to re-interrogate the same elution peak or target compound, while the various embodiments described herein use a sentinel transition to trigger a group of transitions that are aimed at interrogating at least one later elution peak or target compound.

Therefore, a triggering MRM transition of the '479 patent does not trigger a next group of transitions from a contiguous series of groups of transitions with different retention time ranges. Instead, a triggering MRM transition of the '479 patent triggers a group of MRM transitions with the same retention time as the triggering MRM transition. The triggering MRM transition of the '479 patent is also not part of a group that precedes the triggered group in a series of contiguous groups.

Likewise, a sentinel transition of various embodiments described herein does not trigger a group of MRM transitions that all target the same retention time as the sentinel transition. Instead, a sentinel transition of various embodiments described herein triggers a group of MRM transitions that includes at least one MRM transition that targets a retention time or elution peak other than the retention time or elution peak targeted by the sentinel transition.

As described above, because the groups of transitions of various embodiments described herein are not dependent on a specific retention time, workflows based on these systems and methods can be used without modification whenever the separation device changes or the gradient of separation changes. The gradient of separation determines how fast or how slow the targeted compounds of a sample are eluted. If the slope of the gradient of separation is increased, the targeted compounds of a sample are eluted faster, for example.

Figure 3:
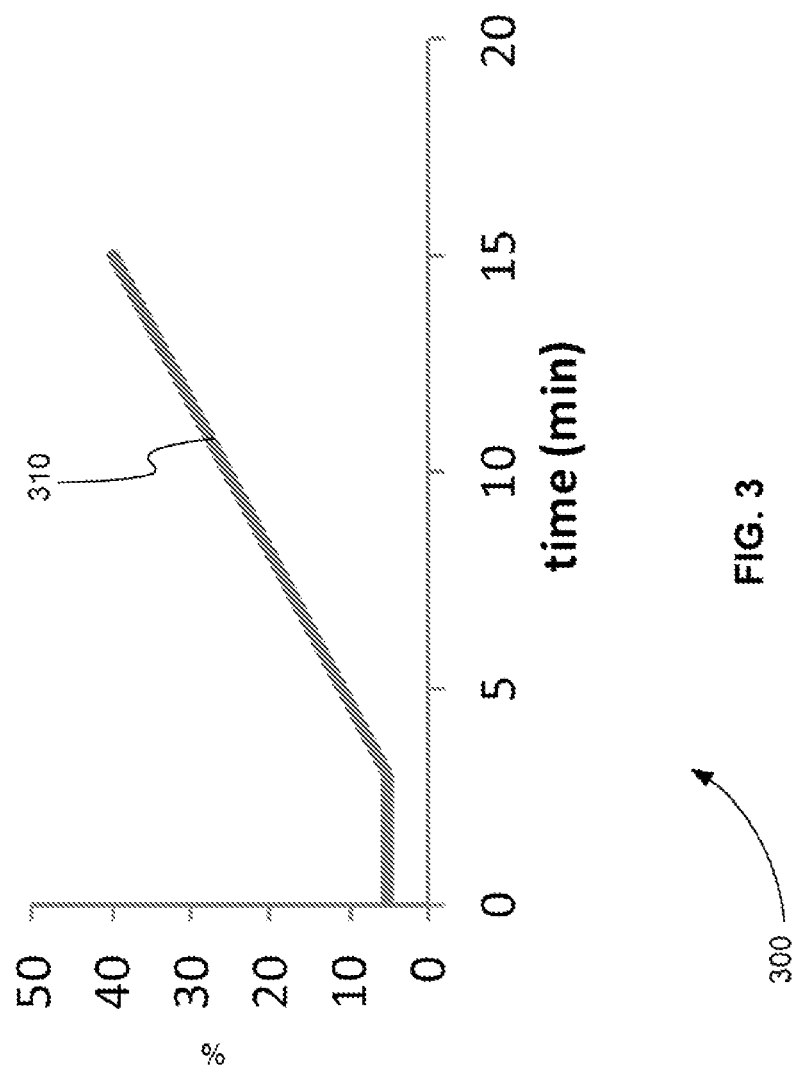
FIG. 3 is an exemplary plot of a gradient of separation, in accordance with various embodiments.

FIG. 3 is an exemplary plot 300 of a gradient of separation, in accordance with various embodiments. Plot 300 describes how the percentage of organic composition of a chromatographic separation device is designed to vary over time. Plot 300 shows that the organic composition varies from 5 to 40% over 15 minutes producing slope 310.

Figure 4:
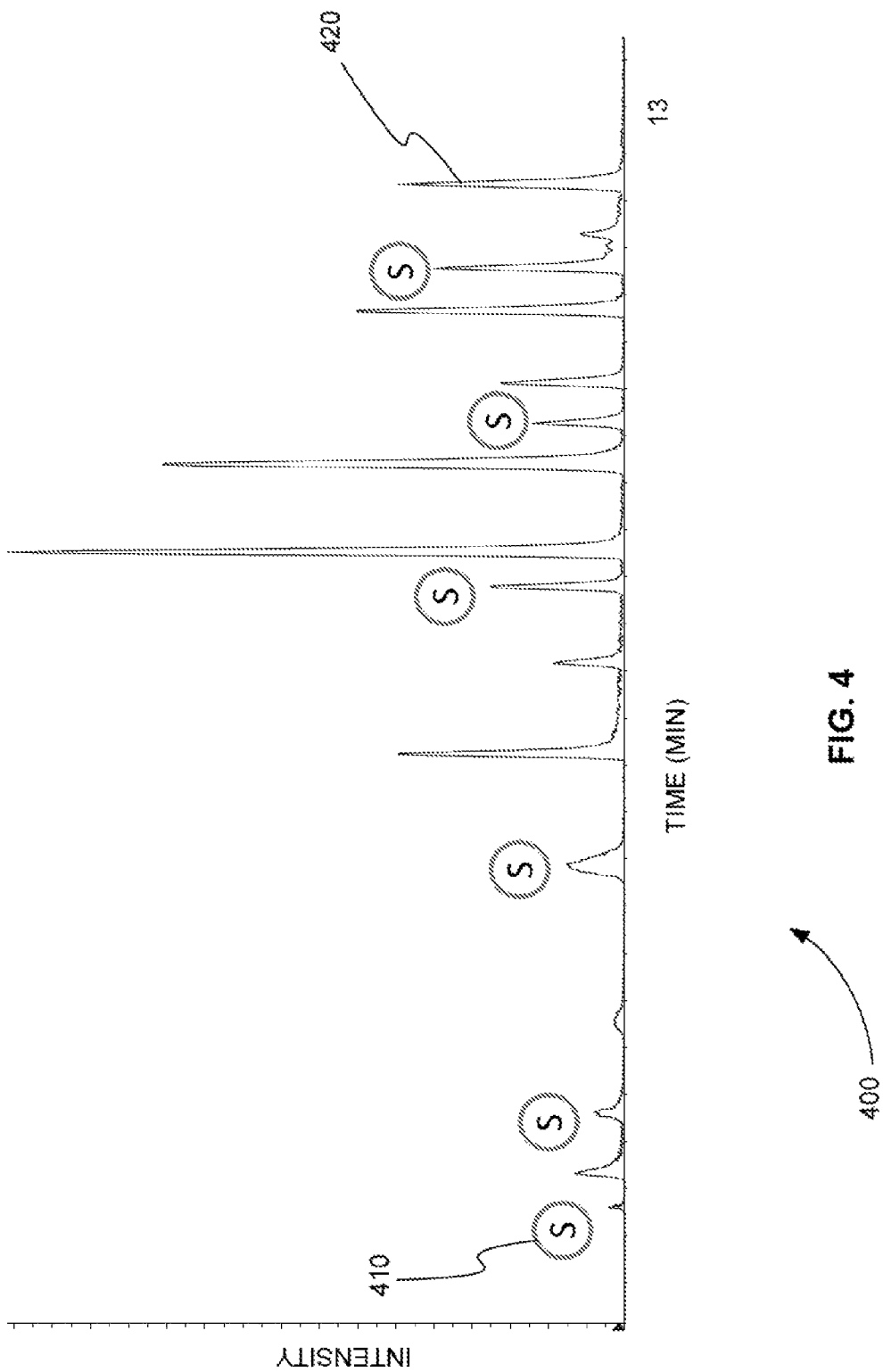
FIG. 4 is an exemplary TIC chromatogram plot showing the product ion peaks produced by a method that used six sentinel transitions to trigger other groups of transitions for a sample that was separated according to the gradient of separation shown in FIG. 3, in accordance with various embodiments.

FIG. 4 is an exemplary TIC chromatogram plot 400 showing the product ion peaks produced by a method that used six sentinel transitions to trigger other groups of transitions for a sample that was separated according to the gradient of separation shown in FIG. 3, in accordance with various embodiments. The locations of the six sentinel transitions are indicated by circles 410 in plot 400.

Figure 5:
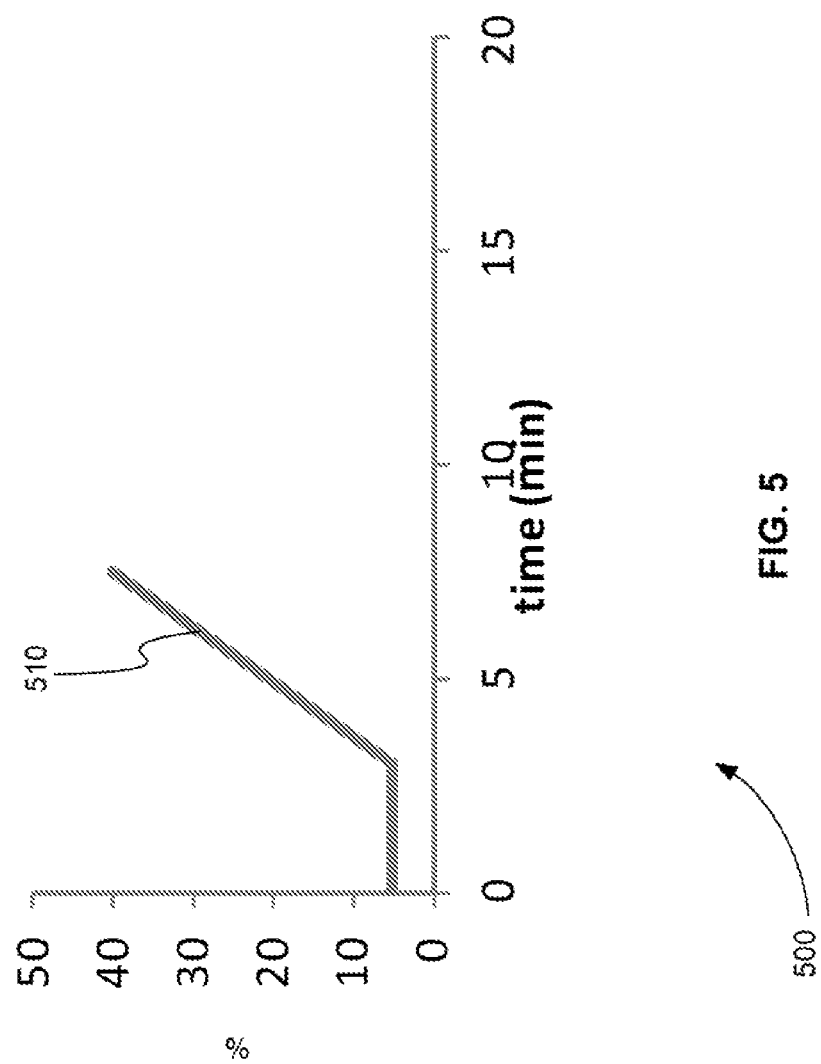
FIG. 5 is an exemplary plot of a gradient of separation that has an increased slope in comparison to the gradient of separation shown in FIG. 3, in accordance with various embodiments.

FIG. 5 is an exemplary plot 500 of a gradient of separation that has an increased slope in comparison to the gradient of separation shown in FIG. 3, in accordance with various embodiments. Plot 500 describes how the percentage of organic composition of a chromatographic separation device is designed to vary over time. Plot 500 shows that the organic composition varies from 5 to 40% over 8 minutes producing slope 510. A comparison of slope 510 with slope 310 of FIG. 3 shows that slope 510 of FIG. 5 is larger than slope 310 of FIG. 3. In other words, the elution described in FIG. 5 is much faster than the elution in FIG. 3.

Figure 6:
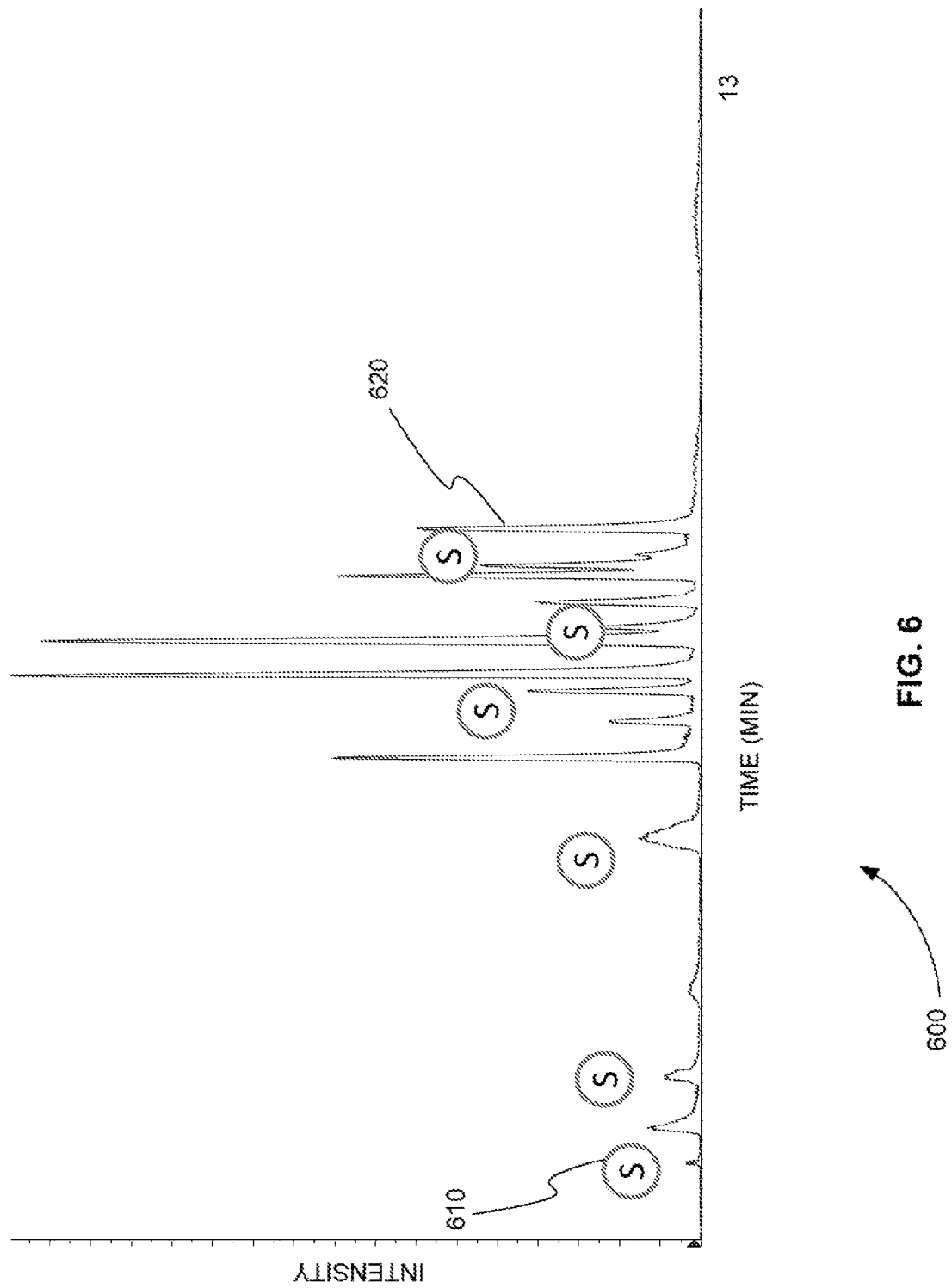
FIG. 6 is an exemplary TIC chromatogram plot showing the product ion peaks produced by a method that used the same six sentinel transitions using to produce FIG. 4 to trigger other groups of transitions for a sample that was separated according to the gradient of separation shown in FIG. 5, in accordance with various embodiments.

FIG. 6 is an exemplary TIC chromatogram plot 600 showing the product ion peaks produced by a method that used the same six sentinel transitions using to produce FIG. 4 to trigger other groups of transitions for a sample that was separated according to the gradient of separation shown in FIG. 5, in accordance with various embodiments. The locations of the six sentinel transitions are indicated by circles 610 in plot 600.

A comparison of FIGS. 4 and 6 shows that as the gradient of separation increases, the product ion peaks are shifted to earlier times. For example, product ion peak 420 in FIG. 4 corresponds to product ion peak 620 in FIG. 6. Product ion peak 420 in FIG. 4 occurs at a retention time of about 12.5 min. Product ion peak 620 in FIG. 6 occurs at a retention time of about 8.0 min.

As described above, using scheduled MRM, the retention times of all of the MRMs would have to be changed when the gradient of separation is increased from the gradient shown in FIG. 3 to the gradient shown in FIG. 5. Otherwise, for example, product ion peak 620 in FIG. 6 would not be found, because the scheduled MRM would be looking for product ion peak 620 at a retention time of 12.5 min.

FIGS. 4 and 6 show that the grouping of MRM transitions by the order of retention time and the use of sentinel transitions allows all product ion peaks to be found even if the gradient of separation increases. In addition, no re-computation of retention time is need for each transition.

System for Triggering a Group of Contiguous Groups of MRM Transitions

Figure 7:
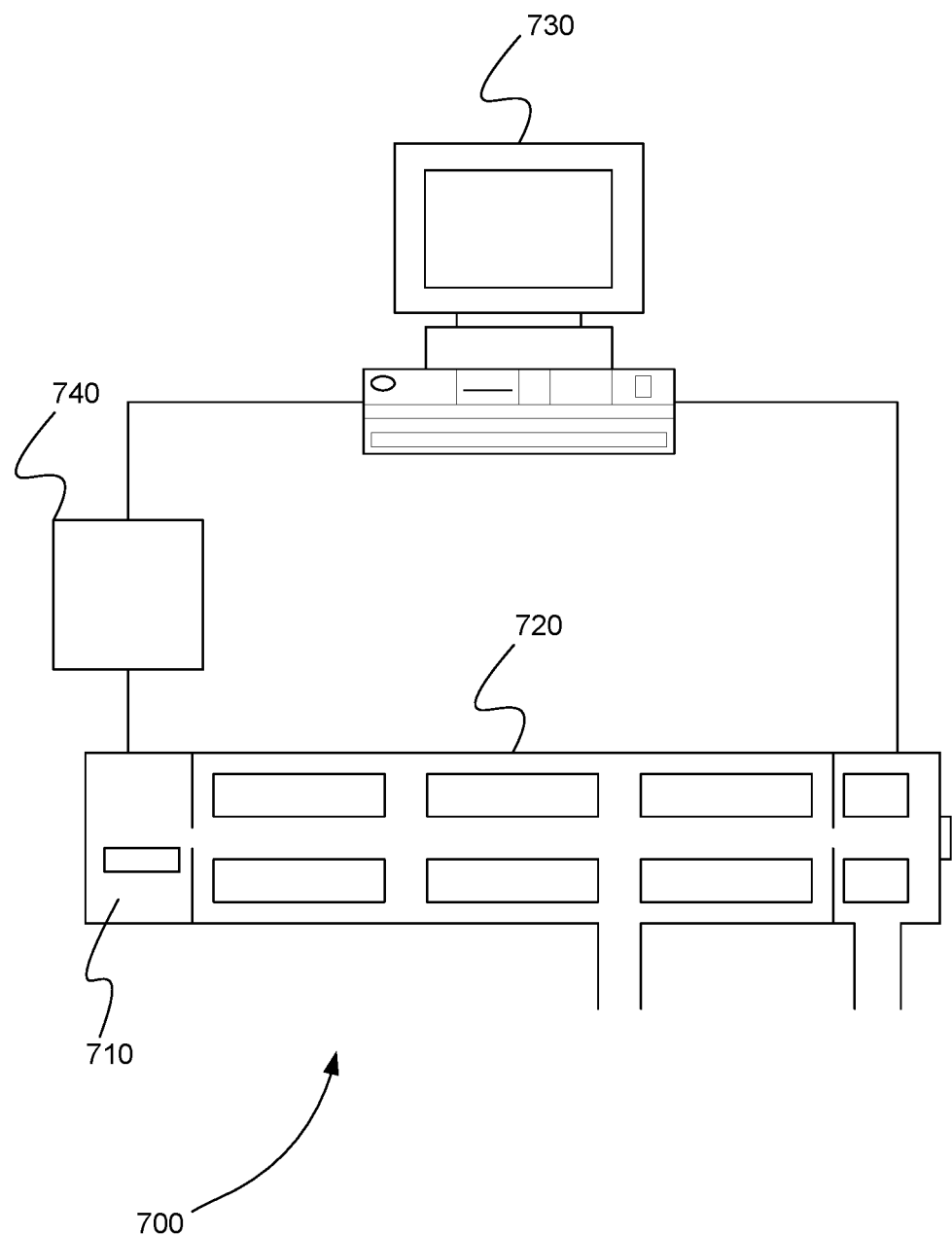
FIG. 7 is a schematic diagram of system for triggering a group of multiple reaction monitoring (MRM) transitions from a series of contiguous groups when at least one sentinel transition of the group is detected as part of a previous group, in accordance with various embodiments.

FIG. 7 is a schematic diagram of system 700 for triggering a group of multiple reaction monitoring (MRM) transitions from a series of contiguous groups when at least one sentinel transition of the group is detected as part of a previous group, in accordance with various embodiments. System 700 includes separation device 740, ion source 710, tandem mass spectrometer 720, and processor 730. Separation device 740 separates one or more compounds from a sample. The sample is a sample mixture, for example. Separation device 740 can separate compound over time using one of a variety of techniques. These techniques include, but are not limited to, ion mobility, gas chromatography (GC), liquid chromatography (LC), capillary electrophoresis (CE), or flow injection analysis (FIA).

Ion source 710 can be part of tandem mass spectrometer 720, or can be a separate device. Ion source 710 ionizes the separated one or more compounds received from separation device 740, producing an ion beam of one or more precursor ions.

Tandem mass spectrometer 720 can include, for example, one or more physical mass filters and one or more physical mass analyzers. A mass analyzer of tandem mass spectrometer 720 can include, but is not limited to, a time-of-flight (TOF), quadrupole, an ion trap, a linear ion trap, an orbitrap, or a Fourier transform mass analyzer.

Tandem mass spectrometer 720 receives the ion beam from ion source 710. For each cycle of a plurality cycles, tandem mass spectrometer 720 executes on the ion beam a series of MRM precursor ion to product ion transitions read from a list. The list is a duty cycle list, for example. For each transition of the series, tandem mass spectrometer 720 selects and fragments a precursor ion of each transition and mass analyzes a small mass-to-charge ratio (m/z) range around the m/z of a product ion of the each transition to determine if the product ion of the transition is detected.

Processor 730 can be, but is not limited to, a computer, microprocessor, or any device capable of sending and receiving control signals and data from tandem mass spectrometer 720 and processing data. Processor 730 can be, for example, computer system 100 of FIG. 1. In various embodiments, processor 730 is in communication with tandem mass spectrometer 720 and separation device 740.

Processor 730 receives a plurality of MRM transitions to be used to interrogate the sample. The plurality of MRM transitions are received from a user, for example. Processor 730 divides the plurality of MRM transitions into two or more contiguous groups of MRM transitions so that different groups can be monitored separately during the plurality of cycles. For example, processor 730 can order the plurality of MRM transitions according to expected retention time. Expected retention times are received for each MRM transition from a user, for example. Processor 730 can then divide the ordered MRM transitions into two or more contiguous groups of MRM transitions so that different groups can be monitored separately during the plurality of cycles.

Processor 730 selects at least one sentinel transition in each group of the two or more contiguous groups that identifies a next group of the two or more contiguous groups that is to be monitored. The at least one sentinel transition identifies or triggers the next adjacent group of the two or more contiguous groups, for example.

Processor 730 places a first group of the two or more contiguous groups on the list of tandem mass spectrometer 720, so that tandem mass spectrometer 720 monitors the MRM transitions of the first group. When at least one sentinel transition of the first group is detected by tandem mass spectrometer 720, processor 730 places a next group of the two or more contiguous groups identified by the sentinel transition on the list.

In various embodiments, each group of the two or more contiguous groups includes MRM transitions that overlap with MRM transitions of at least one other group of the two or more groups in order to ensure correct peak definition. The overlap is with an adjacent group, for example.

In various embodiments, processor 730 further removes the first group from the list, when a sentinel transition of the next group is detected.

In various embodiments, processor 730 further selects a stop sentinel transition for each group of the two or more contiguous groups that identifies a previous group of the two or more contiguous groups. When a stop sentinel transition of a group is detected, processor 730 further removes a previous group identified by the stop sentinel from the list.

In various embodiments, the sentinel transitions for each group of the two or more contiguous groups are monitored as part of each group, or for the entire acquisition. For example, each group of the two or more contiguous groups further includes each sentinel transition of the other groups of the two or more contiguous groups. This allows sentinel transitions to be independent of retention windows also. As a result, tandem mass spectrometer 720 detects a product ion of the each transition without using a retention time window for the each transition.

Alternatively, sentinel transitions can be monitored with wide retention time windows. The groups MRM transitions triggered by sentinel transitions, however, are not monitored according to retention time windows.

Processor 730 can select any of the MRM transitions of a group as the at least one sentinel. For example, processor 730 can select the at least one sentinel transition in each group by selecting an MRM transition of each group with the latest expected retention time. In other words, processor 730 can select the MRM transition at the end of each group as the sentinel transition.

In various embodiments, an MRM transitions can include a precursor ion and/or one or more product ions of the precursor ion that are found in a full scan product ion spectrum. For example, for TOF and orbitrap mass analyzers, tandem mass spectrometer 720 executes on the ion beam a series of precursor ion to full product ion spectrum scans read from a list. The list is a duty cycle list, for example. For each precursor ion of the series, tandem mass spectrometer 720 selects and fragments a precursor ion and mass analyzes an entire mass-to-charge ratio (m/z) range of product ions to determine if the precursor ion is detected. The unfragmented precursor ion and/or one or more product ions of the precursor ion are detected in the full product ion spectrum, for example.

Processor 730 receives a plurality of precursor ions and/or one or more product ions of the precursor ion to be used to interrogate the sample. The plurality of precursor ions and/or one or more product ions of the precursor ion are received from a user, for example. Processor 730 divides the plurality of precursor ions and/or one or more product ions of the precursor ion into two or more contiguous groups of precursor ions and/or one or more product ions of the precursor ion so that different groups can be monitored separately during the plurality of cycles. For example, processor 730 can order the plurality of precursor ions and/or one or more product ions of the precursor ion according to expected retention time. Expected retention times are received for each precursor ion from a user, for example. Processor 730 can then divide the ordered precursor ions and/or one or more product ions of the precursor ion into two or more contiguous groups of precursor ions and/or one or more product ions of the precursor ion so that different groups can be monitored separately during the plurality of cycles.

Processor 730 selects at least one sentinel precursor ion and/or one or more sentinel product ions of the precursor ion in each group of the two or more contiguous groups that identifies a next group of the two or more contiguous groups that is to be monitored. The at least one sentinel precursor ion and/or one or more sentinel product ions of the precursor ion identifies or triggers the next adjacent group of the two or more contiguous groups, for example.

Processor 730 places a first group of the two or more contiguous groups on the list of tandem mass spectrometer 720, so that tandem mass spectrometer 720 monitors the precursor ions and/or one or more product ions of the precursor ion of the first group. When at least one sentinel precursor ion of the first group is detected by tandem mass spectrometer 720, processor 730 places a next group of the two or more contiguous groups identified by the sentinel precursor ion and/or one or more sentinel product ions of the precursor ion on the list.

Method for Triggering a Group of Contiguous Groups of MRM Transitions

Figure 8:
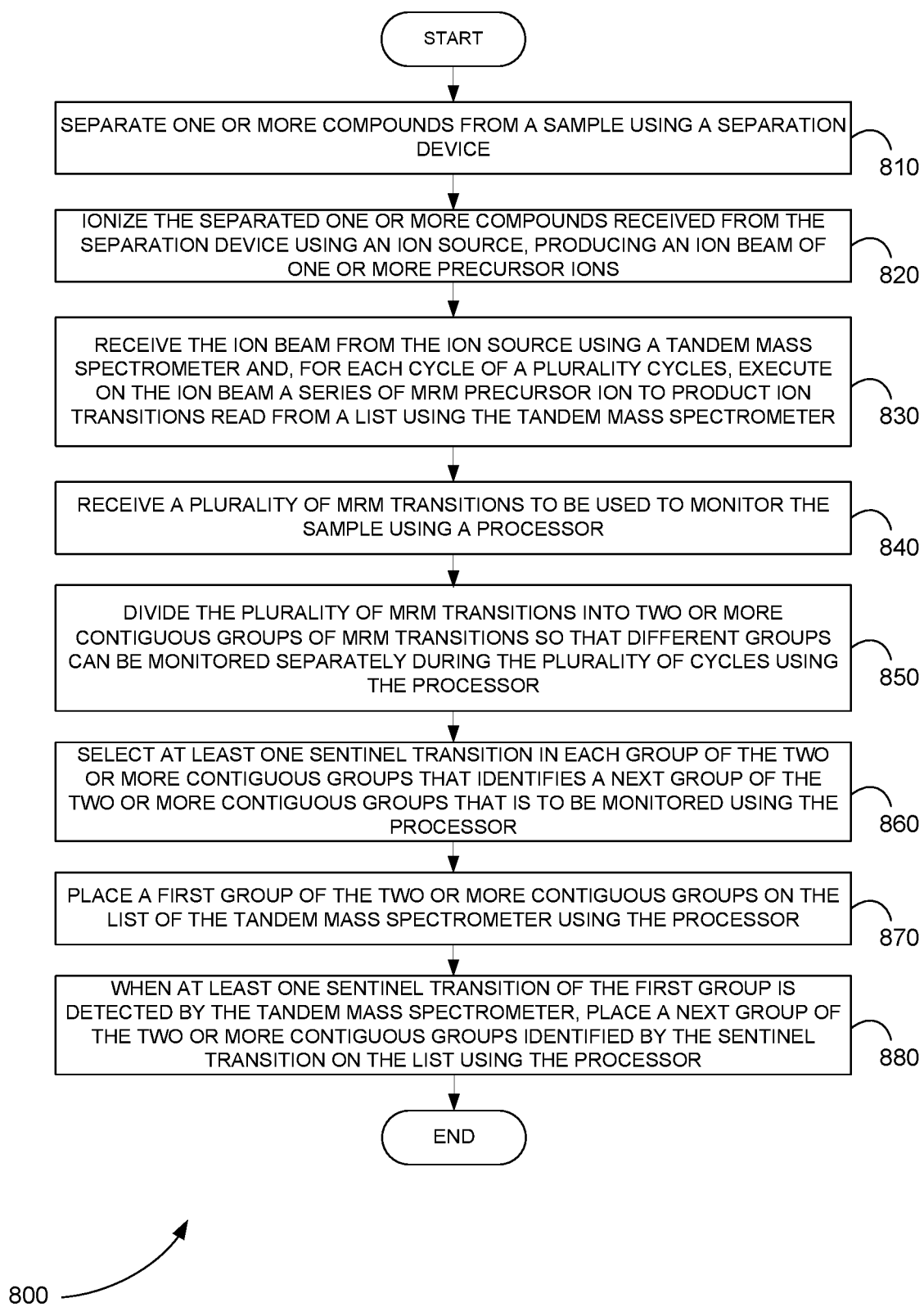
FIG. 8 is a flowchart showing a method for triggering a group of MRM transitions from a series of contiguous groups when at least one sentinel transition of the group is detected as part of a previous group, in accordance with various embodiments.

FIG. 8 is a flowchart showing a method 800 for triggering a group of MRM transitions from a series of contiguous groups when at least one sentinel transition of the group is detected as part of a previous group, in accordance with various embodiments.

In step 810 of method 800, one or more compounds are separated from a sample using a separation device.

In step 820, the separated one or more compounds received from the separation device are ionized using an ion source, producing an ion beam of one or more precursor ions.

In step 830, the ion beam is received from the ion source using a tandem mass spectrometer and, for each cycle of a plurality cycles, a series of MRM precursor ion to product ion transitions read from a list are executed on the ion beam using the tandem mass spectrometer. For each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected.

In step 840, a plurality of MRM transitions to be used to monitor the sample are received using a processor.

In step 850, the plurality of MRM transitions are divided into two or more contiguous groups of MRM transitions so that different groups can be monitored separately during the plurality of cycles using the processor.

In step 860, at least one sentinel transition is selected in each group of the two or more contiguous groups that identifies a next group of the two or more contiguous groups that is to be monitored using the processor.

In step 870, a first group of the two or more contiguous groups is placed on the list of the tandem mass spectrometer using the processor.

In step 880, when at least one sentinel transition of the first group is detected by the tandem mass spectrometer, a next group of the two or more contiguous groups identified by the sentinel transition is placed on the list using the processor.

Computer Program Product for Triggering a Group of Contiguous Groups

In various embodiments, computer program products include a tangible computer-readable storage medium whose contents include a program with instructions being executed on a processor so as to perform a method for triggering a group of MRM transitions from a series of contiguous groups when at least one sentinel transition of the group is detected as part of a previous group. This method is performed by a system that includes one or more distinct software modules.

Figure 9:
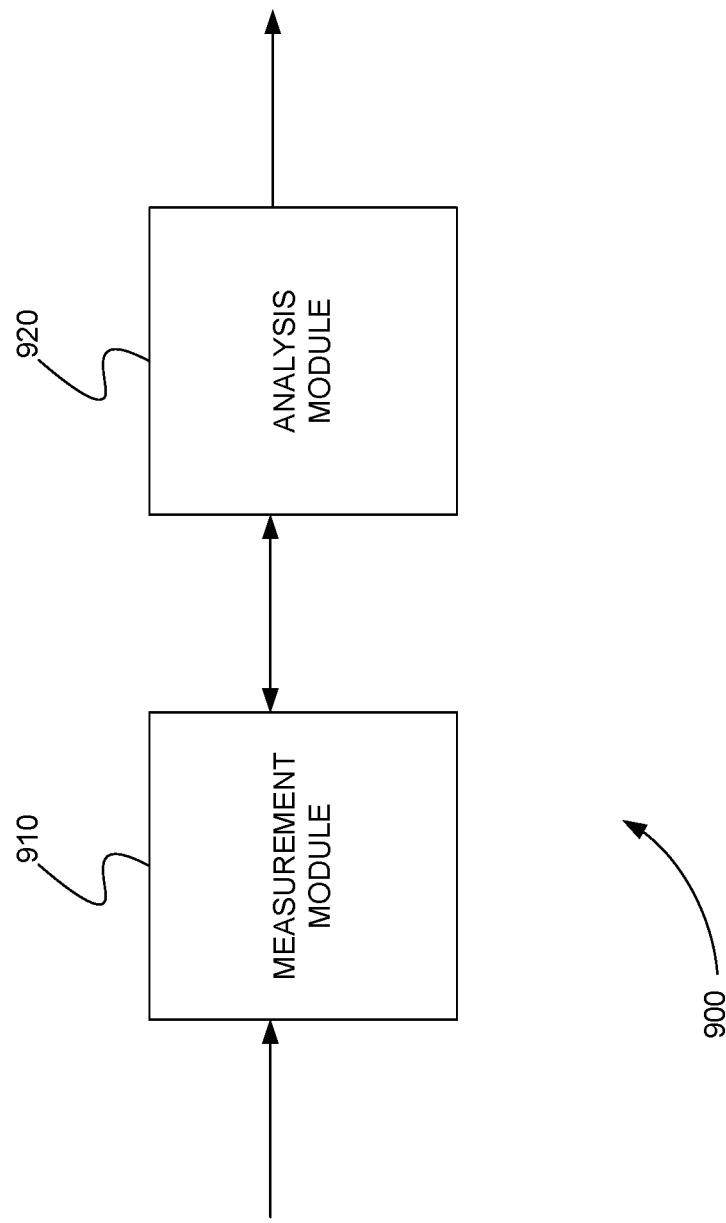
FIG. 9 is a schematic diagram of a system that includes one or more distinct software modules that performs a method for triggering a group of MRM transitions from a series of contiguous groups when at least one sentinel transition of the group is detected as part of a previous group, in accordance with various embodiments.

FIG. 9 is a schematic diagram of a system 900 that includes one or more distinct software modules that performs a method for triggering a group of MRM transitions from a series of contiguous groups when at least one sentinel transition of the group is detected as part of a previous group, in accordance with various embodiments. System 900 includes measurement module 910 and analysis module 920.

For each cycle of a plurality cycles, measurement module 910 instructs a tandem mass spectrometer to execute on an ion beam a series of MRM precursor ion to product ion transitions read from a list. For each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected. The ion beam is produced by an ion source that ionizes one or more compounds separated from a sample using a separation device.

Analysis module 920 receives a plurality of MRM transitions to be used to monitor the sample. Analysis module 920 divides the plurality of MRM transitions into two or more contiguous groups of MRM transitions so that different groups can be monitored separately during the plurality of cycles. Analysis module 920 selects at least one sentinel transition in each group of the two or more contiguous groups that identifies a next group of the two or more contiguous groups that is to be monitored.

Measurement module 910 places a first group of the two or more contiguous groups on the list of the tandem mass spectrometer. When at least one sentinel transition of the first group is detected by the tandem mass spectrometer, measurement module 910 places a next group of the two or more contiguous groups identified by the sentinel transition on the list.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. Similarly, though the described application used MRM as a detection technique, the described method can be applied to any targeted analysis for MS/MS analysis such as MRM3, single ion monitoring (SIM) or even targeted product ion scan (TOF-MS). In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for triggering a group of multiple reaction monitoring (MRM) transitions from a series of contiguous groups when at least one sentinel transition of the group is detected as part of a previous group, comprising:
   a separation device that separates one or more compounds from a sample;
   an ion source that ionizes the separated one or more compounds received from the separation device, producing an ion beam of one or more precursor ions;
   a tandem mass spectrometer that receives the ion beam from the ion source and for each cycle of a plurality cycles executes on the ion beam a series of MRM precursor ion to product ion transitions read from a list, wherein for each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected; and
   a processor in communication with the tandem mass spectrometer that receives a plurality of MRM transitions to be used to monitor the sample,
      divides the plurality of MRM transitions into two or more contiguous groups of MRM transitions so that different groups can be monitored separately during the plurality of cycles,
      selects at least one sentinel transition in each group of the two or more contiguous groups that identifies a next group of the two or more contiguous groups that is to be monitored,
      places a first group of the two or more contiguous groups on the list of the tandem mass spectrometer, and
      when at least one sentinel transition of the first group is detected by the tandem mass spectrometer, places a next group of the two or more contiguous groups identified by the sentinel transition on the list.

2. The system of claim 1, wherein each group of the two or more contiguous groups includes MRM transitions that overlap with MRM transitions of at least one other group of the two or more groups in order to ensure correct peak definition.

3. The system of claim 1, wherein the processor further removes the first group from the list, when a sentinel transition of the next group is detected by the tandem mass spectrometer.

4. The system of claim 1, wherein the processor further selects a stop sentinel transition for each group of the two or more contiguous groups that identifies a previous group of the two or more contiguous groups, and when a stop sentinel transition of an group is detected, the processor further removes a previous group identified by the stop sentinel from the list.

5. The system of claim 1, wherein each group of the two or more contiguous groups further includes each sentinel transition of the other groups of the two or more contiguous groups.

6. The system of claim 1, wherein the tandem mass spectrometer detects a product ion of the each transition without using a retention time window for the each transition.

7. The system of claim 1, wherein the processor selects the at least one sentinel transition in each group by selecting an MRM transition of the each group with the latest expected retention time.

8. A method for triggering a group of multiple reaction monitoring (MRM) transitions from a series of contiguous groups when at least one sentinel transition of the group is detected as part of a previous group, comprising:

separating one or more compounds from a sample using a separation device;

ionizing the separated one or more compounds received from the separation device using an ion source, producing an ion beam of one or more precursor ions;

receiving the ion beam from the ion source using a tandem mass spectrometer and, for each cycle of a plurality cycles, executing on the ion beam a series of MRM precursor ion to product ion transitions read from a list using the tandem mass spectrometer, wherein for each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected;

receiving a plurality of MRM transitions to be used to monitor the sample using a processor;

dividing the plurality of MRM transitions into two or more contiguous groups of MRM transitions so that different groups can be monitored separately during the plurality of cycles using the processor;

selecting at least one sentinel transition in each group of the two or more contiguous groups that identifies a next group of the two or more contiguous groups that is to be monitored using the processor;

placing a first group of the two or more contiguous groups on the list of the tandem mass spectrometer using the processor; and when at least one sentinel transition of the first group is detected by the tandem mass spectrometer, placing a next group of the two or more contiguous groups identified by the sentinel transition on the list using the processor.

9. The method of claim 8, wherein each group of the two or more contiguous groups includes MRM transitions that overlap with MRM transitions of at least one other group of the two or more groups in order to ensure correct peak definition.

10. The method of claim 8, further comprising when a sentinel transition of the next group is detected by the tandem mass spectrometer, removing the first group from the list using the processor.

11. The method of claim 8, further comprising selecting a stop sentinel transition for each group of the two or more contiguous groups that identifies a previous group of the two or more contiguous groups using the processor, and when a stop sentinel transition of an group is detected, further removing a previous group identified by the stop sentinel from the list using the processor.

12. The method of claim 8, wherein each group of the two or more contiguous groups further includes each sentinel transition of the other groups of the two or more contiguous groups.

13. The method of claim 8, wherein a product ion of the each transition is detected without using a retention time window for the each transition using the tandem mass spectrometer.

14. The method of claim 8, further comprising selecting the at least one sentinel transition in each group by selecting an MRM transition of the each group with the latest expected retention time.

15. A computer program product, comprising a non-transitory and tangible computer-readable storage medium whose contents include a program with instructions being executed on a processor so as to perform a method for triggering a group of multiple reaction monitoring (MRM) transitions from a series of contiguous groups when at least one sentinel transition of the group is detected as part of a previous group, comprising:

providing a system, wherein the system comprises one or more distinct software modules, and wherein the distinct software modules comprise a measurement module and an analysis module;

for each cycle of a plurality cycles, instructing a tandem mass spectrometer to execute on an ion beam a series of MRM precursor ion to product ion transitions read from a list using the measurement module, wherein for each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected and wherein the ion beam is produced by an ion source that ionizes one or more compounds separated from a sample using a separation device;

receiving a plurality of MRM transitions to be used to monitor the sample using the analysis module;

dividing the plurality of MRM transitions into two or more contiguous groups of MRM transitions so that different groups can be monitored separately during the plurality of cycles using the analysis module;

selecting at least one sentinel transition in each group of the two or more contiguous groups that identifies a next group of the two or more contiguous groups that is to be monitored using the analysis module;

placing a first group of the two or more contiguous groups on the list of the tandem mass spectrometer using the measurement module; and when at least one sentinel transition of the first group is detected by the tandem mass spectrometer, placing a next group of the two or more contiguous groups identified by the sentinel transition on the list using the measurement module.

* * * * *